United States Patent [19]

Collins et al.

[11] Patent Number: 4,938,961

[45] Date of Patent: Jul. 3, 1990

[54] ORGAN PRESERVATION SOLUTION CONTAINING POKYETHYLENE GYCOL AND METHOD OF PERFORMING CARDIOPLEGIA

[76] Inventors: Geoffrey Collins, 14 Leeward Rd., Belvedere, Calif. 94920; Winston Wicomb, 38 Yolo St., Corte Madera, Calif. 94925

[21] Appl. No.: 345,121

[22] Filed: Apr. 28, 1989

[51] Int. Cl.$^5$ ............... A61H 31/08; A61H 33/42; A61H 31/765; A61H 37/02

[52] U.S. Cl. ............... 424/606; 424/679; 424/680; 514/2; 514/61; 514/53; 514/723

[58] Field of Search ............... 424/606, 679, 680; 514/2, 61, 53, 723

[56] References Cited

U.S. PATENT DOCUMENTS 3,450,502  6/1969  Hymes ............... 514/723

FOREIGN PATENT DOCUMENTS

PCT/US86/-
02022  4/1987  PCT Int'l Appl.

OTHER PUBLICATIONS

Chambers et al., Cardiovascular Res., 1989 23(4) 351-8 Chemical Age vol. 110, 1989, Abstract 225260.

Mees, N., Southard, J. and Belzer, F., Inhibition of Ischemic Induced Cellular Swelling in Kidney Cortex Tissue by Lactobionate Anions, J. Trauma, vol 22, No. 2, Feb. 1982, pp. 118-120.

Southard, J. and Belzer, F., Control of Canine Kidney Cortex Slice Volume and Ion Distribution at Hypothermia by Impermeable Anions, Cryobiology 17, 540-548 (1980).

Wahlberg, J., Southard, J., and Belzer, F., Development of a Cold Storage Solution for Pancreas Preservation, Cryobiology 23, 477-482 (1986).

Wahlberg, J., Love, R., Landegaard, L., Southard, J., and Belzer, F., 72-Hour Preservation of the Canine Pancreas, Transplantation 43, 5-8 (1987).

Ploeg, R., Coossens, D., McAnulty, J., Southard, J., and Belzer, F., Successful 72-Hour Cold Storage of Dog Kidneys with UW Solution, Transplantation 46, 191-196 (1988).

Jamieson, N., et al., Preservation of the Canine Liver for 24-48 Hours Using Simple Cold Storage with UW Solution, Transplantation 46, 517-522 (1988).

Jamieson, N., et al., An Analysis of the Components in UW Solution Using the Isolated Perfused Rabbit Liver, Transplantation 46, 512-516 (1988).

Collins, G., et al., Beneficial Effect of Low Concentrations of Cryoprotective Agents on Short-Term Rabbit Kidney Perfusion, Cryobiology 21, 246-249 (1984).

Bennett, J., et al., The Effects of Oxygen Free Radicals on the Preserved Kidney, Cryobiology 24, 264-269 (1987).

Martin D., et al., Experimental Renal Preservation, U. Urology 103, 681-685 (1970).

Hermann, T., et al., Preservation of Canine Kidneys by Hypothermia and Low Flow Perfusion with Bloodless Perfusate, Arch. Surg. 98, 127—127 (1969).

Calne, R., et al., Trickle Perfusion for Organ Preservation, Nature, 235, 171-174 (1972).

Suzuki, S., et al., Twenty-four Hour Preservation of canine Hearts by Retrograde Coronary Sinus Perfusion, J. Heart Transplantation, IV, 76-80 (1984).

Wicomb, W., et al., Ex Vivo Function Evaluation of Pig Hearts Subjected to 24 Hours' Preservation by Hypothermic Perfusion, S. Afr. Med. J. 60, 245-248 (1981).

Belzer, F., et al., Principles of Solid-Organ Preservation by Cold Storage, Transplantation 45, 673-676 (1988).

Daniel, M., Factors Influencing the Survival of Cell Monolayers During Storage at 4°, Br. J. exp. Path. 57, 137-147 (1976).

Ganote, C., et al., Cellular Swelling and Irreversible Myocardial Injury, Am. J. Path. 88, 95-118 (1977).

Primary Examiner—Mukund J. Sham
Assistant Examiner—E. C. Ward
Attorney, Agent, or Firm—James R. Haller; Gregory P. Kaihoi; Mary P. Bauman

[57] ABSTRACT

An organ preservation solution, particularly valuable in the preservation of mammalian hearts intended for transplantation, in aqueous solution, at least about 3% by weight of polypropylene glycol having an average molecular weight of at least about 15,000 daltons and being free of material retained by 10 micron filtration, a buffer buffering the pH of the solution perfusate to a value in the range of about 7.1 to about 7.5, and an impermeant composition for retarding the passage of water across cell membranes of an organ treated with the solution.

16 Claims, No Drawings

ORGAN PRESERVATION SOLUTION CONTAINING POKYETHYLENE GYCOL AND METHOD OF PERFORMING CARDIOPLEGIA

FIELD OF THE INVENTION

The invention relates to aqueous organ preservation solutions and methods useful in surgical operations on the heart and in transplantation of the heart and other mammalian organs.

BACKGROUND OF THE INVENTION

Transplantation of vital organs such as the heart, liver, kidney, pancreas, and lung has become increasingly successful and sophisticated in recent years. Because mammalian organs progressively lose their ability to function during storage, even at ice temperatures, transplant operations need to be performed expeditiously after organ procurement so as to minimize the period of time that the organ is without supportive blood flow. This is particularly true for the heart in which the permissible storage time with present methods of preservation is limited to a maximum of about 4 to 6 hours.

In clinical practice, the two situations in which cardiac preservation is required are heart transplantation and cardioplegia for open heart surgery. In heart transplantation, the donor heart is exposed through a midline sternotomy. After opening the pericardium, the superior and inferior vena cavae and the ascending aorta are isolated. The venous inflow is then occluded, the aorta is cross clamped, and approximately 1 liter of cold cardioplegic solution is flushed into the aortic root under pressure through a needle. As a result, the heart is immediately arrested, and cooling is supplemented by surrounding it with iced saline. The cold arrested heart is then surgically excised, immersed in cold cardioplegic solution, surround by ice and rushed to the recipient center.

The recipient's chest is opened through a midline sternotomy, and after placing the patient on cardiopulmonary bypass, the diseased heart is excised. The preserved donor heart is then removed from the preservation apparatus, trimmed appropriately and sewn to the stumps of the great vessels and the two atria in the chest. After completion of the vascular anastomoses, blood is allowed to return to the heart. It then will either resume beating spontaneously or will require chemical and electical treatment to restore normal rhythm. When the heart is ready to take over the circulation, the cardiopulmonary bypass is discontinued and the recipient's chest closed.

Most non transplant surgical procedures on the heart, such as coronary artery bypass grafting, require that the heart's action be arrested for a period ranging from 1 to 4 hours. During this time, the heart is kept cool by external cooling as well as by periodic reflushing a cardioplegic solution through the coronary arteries. The composition of the latter solution is designed to rapidly arrest the heart and to keep it in good condition during the period of standstill so that it will resume normal function when the procedure is finished.

In the cardioplegic procedure, the heart is exposed in the chest, and as a minimum the aortic root is isolated. A vascular clamp is applied across the aorta and approximately 1 liter of cold cardioplegic solution is flushed into the aortic root through a needle. Venting is provided through the left ventricle, pulmonary artery or the right atrium and the effluent which may contain high levels of potassium is sucked out of the chest. This, together with external cooling, produces rapid cessation of contractions. During the period of arrest, the patient's circulation is maintained artificially using cardiopulmonary bypass.

After completion of the surgical procedure, blood flow is restored to the coronary circulation and beating either returns spontaneously or after chemical and electric treatment. The ease with which stable function is restored depends to a large extent on the effectiveness of preservation by the cardioplegic solution. Once the heart is beating satisfactorily, cardiopulmonary bypass is discontinued and the chest closed.

It is generally understood that "living" organs, including the heart, continue the process of metabolism after removal from the donor so that cell constituents are continuously metabolized to waste products. The accumulation of these metabolic waste products, depletion of cell nutrients and consequent derangement of cell composition lead to progressive loss of function and ultimately to cell death if the storage technique is inadequate. That is, the organ will lose its ability to function adequately after transplantation into the recipient. Several procedures have been successfully explored to enable organs to be preserved ex vivo for useful time periods. In one method the organ to be transplanted is rapidly cooled by flushing cold solutions through the organ's vascular system and maintaining the organ at temperatures near 0° C. for the purpose of greatly slowing the metabolic rate. In the case of the mammalian heart, the flush solution composition is designed to cause the heart to rapidly stop beating as well as to preserve it.

Another method for organ storage utilizes continuous perfusion at temperatures in the range of 7°-10° C. with an oxygenated solution designed to support oxidative metabolism and to remove waste products. A suitable perfusate is delivered through the circulatory system of the isolated organ—usually from the arterial side—and as the perfusate is conveyed through the vascular system waste products are carried away from the organ. Kidneys and livers can commonly be preserved in this manner for several days. However, only limited success has been achieved in preserving the heart, and therefore this method is not used in clinical heart transplantation. The heart must function well enough to sustain a good circulation in the recipient immediately after the transplant operation, whereas some impairment of function can be tolerated in transplanted livers and kidneys. Since hearts can only be preserved for 4-6 hours using cardioplegic solutions, heart transplantation tends to be ruled out in certain situations in which the proposed donor and recipient are far distant from one another.

The viability of a preserved organ depends on a number of factors, among which may be listed (1) cell swelling which occurs at low temperatures as water is transferred across cell membranes in a stored organ, (2) the degree of intracellular acidosis which occurs during non perfused ice storage as a consequence of continued cell metabolism, (3) derangement of internal cell composition which results from impaired metabolism, particularly with respect to cations such as calcium, potassium, magnesium and sodium, and (4) injury caused by oxygen-derived free radicals during oxygenated perfusion or after restoration of the circulation.

Perfusate solutions containing hydroxyethyl starch ("HES") have been reported by Belzer and Southard in *Transplantation,* 45:673 676, April, 1988, for use in preserving the kidney, liver and pancreas. See also PCT Publication No. WO 87/01940 (published Apr. 9, 1987). The compositions differ depending on whether they are to be used for continuous perfusion or a single flush ice storage of the organ. In both cases, however, a central feature of the solution is the content of the colloid HES.

SUMMARY OF THE INVENTION

We have found that mammalian organs, and particularly hearts, can be preserved for comparatively long periods of time without significant loss in viability through the use of aqueous preservation solutions containing polyethylene glycol having a molecular weight above about 15,000 daltons. The solution ingredients, including an impermeant composition, are pharmacologically acceptable, and the solution desirably is buffered to a pH in the range of from about 7.1 to about 7.5. The polyethylene glycol is free of material capable of being removed by filtration through a 10 micron filter. It further has been found that a solution of the type described can be used for heart preservation as a perfusate in a process in which the perfusate is flowed through the circulatory system of a heart muscle at a low flow rate not exceeding about 6 ml per gram of heart weight per hour. The solution may be used for cardioplegia applications, and 4 hours of cardioplegic heart preservation can be achieved without significant loss of viability

DESCRIPTION OF THE PREFERRED EMBODIMENTS

The polyethylene glycol ingredient of solutions of the instant invention has an average molecular weight that is at least about 15,000 daltons and preferably is in the range of from about 15,000 to about 20,000 daltons. The high molecular weight polyethylene glycol desirably may be made through a process in which hydroxy-functional lower molecular weight polyethylene glycols are linked together using, as linking moieties, such diepoxidies as the diglycidyl ether of Bisphenol A. When polyethylene glycol having an average molecular weight of about 8000 daltons is linked in this manner, the resulting material will include some polymer having an average molecular weight of about 8000 daltons, some polymer having an average molecular weight of about 16,000 daltons, and some higher molecular weight polymers generally thought to be multiples of the 8000 dalton material. The initial 8000 dalton material, of course, itself has a molecular weight distribution, and as a result the high molecular weight polyethylene glycol used in the invention has a broad molecular weight distribution. At least about 60 weight percent of the high molecular weight polyethylene glycol, however, is about 15000 daltons or greater in molecular weight. High molecular weight polyethylene glycol is available commercially, as from Union Carbide Corporation.

Of importance, the polyethylene glycol ingredient must be free of particulate or other material that is retained on a 10 micron (preferably a 5 micron) filter. During development of the instant invention, it was found that polyethylene glycol of the type described may contain particulate or gel or other material which, when employed in a perfusion operation, tends to block capillary flow, leading to rapid loss of viability of the organ being treated. The polyethylene glycol ("PEG") is water soluble, and commonly is dissolved at a low concentration in water, following which the solution may be filtered through appropriate filters such as Millipore brand filters to remove the unwanted material. Various filtering methods can be employed. In a preferred embodiment, the polyethylene glycol solution is filtered through ten micron filters and preferably two or more such filters in series. The purpose of the filtration step is to remove particulate or gel or other material that is harmful to organ preservation. Filtration of the PEG solution through 0.2 micron cartridge filters has the additional advantage of rendering the solution bacteriologically sterile.

Desirably, the concentration of the PEG in organ preservation solutions of the invention is maintained in the range of about 4% to about 10% by weight. The desirable effects which are provided by the PEG material are displayed for the most part at concentrations of about 3% by weight or greater. On the other hand, the PEG employed in the instant invention is of sufficiently high molecular weight as to unduly increase the viscosity of an aqueous perfusate solution when the PEG is employed in concentrations exceeding about 10% by weight. Approximately 5% PEG concentrations have yielded excellent results.

The high molecular weight polyethylene glycol employed in the instant invention provides perfusion and cardioplegic flush solutions with unexpectedly good organ preservation capabilities. Although it is believed that in some applications the polyethylene glycol functions as a colloid to keep the perfusate in the vascular system, and that it may interact in some beneficial way with cell membranes, the precise technical explanation for the surprisingly beneficial properties of this material in organ preservation is not known.

The perfusates of the invention may include a variety of further ingredients common to organ preservation, e.g., perfusate solutions in general. Typical ingredients include:

| Ingredient | Amount | Function |
|---|---|---|
| NaOH | 30–40 mM | Provide buffering of ingredients to desired pH |
| Lactobionic acid | 100 mM | Impermeant anion, chelation of calcium and iron |
| KH$_2$PO$_4$ | 25 mM | Provides potassium and phosphate for buffering |
| KOH | 100 mM | Potassium to prevent loss of intracellular cation and for cardioplegia, OH neutralizes lactobionic acid |
| Impermeant non-electrolyte, typically raffinose | 30 mM | Further impermeant to control cell swelling |
| Glutathione | 3 mM | Control of redox potential and protection against free radical injury |

The solution preferably is devoid of nutrients that are metabolized by the organ to be preserved.

EXAMPLE 1

This example describes the use of an organ preservation solution of the invention for cardioplegia and short term heart preservation in an experimental model designed to imitate the conditions of open heart surgery likely to be encountered clinically in operations on the arrested heart. The test was conducted at 15° C. to simulate realistic conditions.

Candidate cardioplegic solutions were prepared as shown in the following Table 1 in which a solution of the invention was designated Solution "A". Solution "B" was the well known and widely used St. Thomas II solution commonly employed in human heart surgery and for cardiac transplantation. Solution "C" was a perfusate solution containing hydroxyethyl starch ("HES") commonly known as the "UW" solution and reported in *Heart Transplantation* 7:456, 1988.

TABLE 1

| Ingredient | Solution A | Solution B | Solution C |
|---|---|---|---|
|  | mM | mM | mM |
| Na (as NaOH) | 40 | 120 | 30 |
| K (as KOH) | 125 | 16 | 125 |
| Ca | — | 1.2 | — |
| Mg | 5 | 16 | 5 |
| $H_2PO_4$ | 25 | — | 25 |
| $SO_4$ | 5 | — | 5 |
| Lactobionate | 100 | — | 100 |
| Raffinose | 30 | — | 30 |
| Cl | — | 160 | — |
| $HCO_3$ | — | 10 | — |
| Polyethylene glycol[1] | 50 Gm/L | — | — |
| HES | — | — | 50 Gm/L |
| Adenosine | — | — | 5 |
| Glutathione | 3 | — | 3 |
| Allopurinol | — | — | 1 |
| Insulin | — | — | 100 Units |
| Penicillin | — | — | .133 Gm/L |
| Dexamethasone | — | — | .008 Gm/L |

[1] Polyethylene glycol compound "20M", Union Carbide Corporation.

New Zealand white rabbits weighing 2-3 kgs were anesthetized using sodium pentobarbital, and supported on a ventilator via a trachesotomy. A median sternotomy was performed and the heart rapidly excised (5-10 sec) and immersed in iced saline. An occlusive cannula was immediately placed in the aorta, and 15-25 ml of one of the above cardioplegic solutions were infused (4° C.) at a pressure of 100 cm $H_2O$. Thereafter, hearts were kept in a water bath at 15° C. for a total of 4 hours. During the first two hours, each heart was reflushed with the cardioplegic solution every 30 minutes in order to simulate clinical practice in which the arrested heart is reflushed approximately every 30 minutes.

After the preservation period, the aorta and left atrium (LA) were cannulated and the hearts were functionally evaluated on an ex vivo perfusion circuit filled with oxygenated Krebs Henseleit solution at 37° C. The test apparatus was similar to that originally described by Neely, et al. (Neely J. R., Liebermeister H., Battersby E. J., et al. Am. J. Physiol. 1967; 212: 804). The hearts were allowed 15 minutes of recovery while on retrograde Langendorff perfusion at a pressure of 100 cm $H_2O$. This was converted to a working heart mode for a 45-minute test period: The LA pressure was kept at 20 cm $H_2O$ and the aortic outflow was connected to a column in which the overflow was set at 100 cm $H_2O$. Measurements of aortic pressure, coronary and aortic flow rates were made and recorded at 1 hour and cardiac output was calculated.

Hearts preserved by each of the three cardioplegic solutions were tested for cardiac output as described above, and that output was compared to the cardiac output of hearts flushed with each of these solutions and tested immediately with no storage period. The observed results were as follows:

TABLE 2

| Candidate Cardioplegic Solution | | Mean Cardiac Output, ml/g (No. of Hearts Tested) |
|---|---|---|
| Control | Solution A | 38.30 ± 2.42 (6) |
| (no | Solution B | 20.51 ± 8.26 (5) |
| storage) | Solution C | 26.47 ± 2.27 (6) |
| Test | Solution A | 37.00 ± 6.53 (5) |
| (4 hour | Solution B | 17.40 ± 0.86 (4) |
| storage) | Solution C | 27.80 ± 11.07 (5) |

Tetrazolium staining revealed diffuse macroscopic infarcts in all hearts treated with Solution B and in one of the 5 hearts treated with Solution C. No infarcts were observed in any of the control hearts, or in any of the test hearts treated with Solution A. The results indicate that the solution of the invention provided substantially improved protection of hearts from injury under realistic conditions in comparison with conventional cardioplegic solutions.

EXAMPLE 2

This example describes the use of an organ preservation solution of the invention employed in a technique involving continuous hypothermic perfusion at very slow rates.

New Zealand white rabbits weighing 2-3 kgs were each anesthetized using sodium pentobarbital, and supported on a ventilator via a tracheostomy. Median sternotomies were performed and the hearts excised and immersed in iced-saline. An occlusive cannula was immediately placed in the aorta of each heart, and 15-25 ml of flush solution infused (4° C.). Extraneous tissue was removed and each heart was rapidly weighed.

The aorta of each heart was tied to a cannula fitted through the lid of a small plastic specimen container in order to stabilize it during the subsequent perfusion period. The container was provided with an outlet port to permit effluent to escape, assuring that the aortic root remained stable and the aortic valve shut so that perfusate passed through the coronary vessels rather than the aortic valve.

Control groups consisted of (a) 6 unstored hearts which had been rapidly removed cooled and arrested with "UW" (a hydroxyethyl starch perfusate reported in Table 3 below) and then immediately functionally evaluated, (b) 6 unstored hearts cooled and arrested with a solution identical to the UW solution but containing polyethylene glycol of molecular weight approximately 15,000-20,000 daltons in place of hydroxyethyl starch, (c) 9 hearts treated as in group (a) and then ice stored for 24 hours, and (d) 11 hearts subjected to low pressure oxygenated perfusion with a cardioplegic solution designated "WP" (Table 3).

Hearts in the experimental groups were perfused at a rate of 3-6 ml/Gm/24 hours with the perfusates reported in Table 3 below. This very low delivery rate was achieved by the use of electrically driven syringe pumps or IV infusion pumps. The solutions were maintained at 0° C. Ten hearts (Experimental group (1)) were perfused with UW solution prepared within 24 hours of use. Experimental group (2) (16 hearts) were perfused with UW solution which had been shelf stored in double plastic bags for 4-6 months. Experimental group (3) (5 hearts) were perfused with UW solution containing no hydroxyethyl starch and Experimental Group (4) (14 hearts) were perfused with the UW solution in which the hydroxyethyl starch had been replaced with 5% polyethylene glycol of molecular weight in the range of approximately 15,000 to 20,000 daltons. The high molecular weight polyethylene glycol reported in this example was that identified in Example 1. In each case, the penicillin, dexamethasone and insulin were added immediately before use. The high molecular weight polyethylene glycol ingredient had been dissolved in water and passed three times through 10 micron Millipore brand filters to remove small amounts of contaminants. Finally, 6 hearts (Experimental Group 5) were perfused with the solution of Experimental Group 4 from which the insulin, penicillin, dexamethasone, adenosine and allopurinol had been omitted. After the 24-hour perfusion period, the aorta and left atrium were cannulated and the hearts were functionally evaluated at 37° C. on an ex vivo perfusion circuit as described in Example 1.

The individual results are summarized in Table 4. The significance of the experimental group data was compared with fresh controls, groups (a) and (b), and 24-hour UW perfused hearts, group (1). The group (a) hearts achieved a cardiac output ("CO") of $26.48\pm2.25$ ml/Gm/min. This was significantly inferior to the CO of group (b) ($38.30\pm2.42$ ml/Gm/min) indicating that the high molecular weight polyethylene glycol solution was superior to the standard UW solution (group (a)) for short term cardioplegia. Those hearts undergoing oxygenated perfusion with WP solution, group (d), had a mean CO of $21.19\pm6.20$. This was significantly inferior to the CO of hearts perfused slowly for 24 hours with UW solution and the two high molecular weight polyethylene glycol solutions (Experimental Groups (1), (4) and (5)), respectively. Hearts perfused slowly with solution containing HES as the colloid showed excellent function after storage (CO $28.72\pm7.69$), indistinguishable from unstored control group (a) but significantly inferior to the high molecular weight polyethylene glycol control group (b). The high molecular weight polyethylene glycol perfusate led to a CO after 24-hour perfusion ($31.52\pm4.49$ group (4), and $31.67\pm3.43$ group (5)) that was actually significantly higher than the HES-UW fresh controls (group a). However, all of experimental groups (1,4, and 5) showed a significantly lower CO after 24-hour perfusion than was found in the fresh polyethylene glycol solution controls (group (b)). This implies that there was a measurable amount of loss of function after 24-hour storage by comparison with the best control group (group (b)).

Omitting the HES or polyethylene glycol colloid from the UW solution was very detrimental in this model. The mean CO in Exp. group (3) fell to $11.44\pm5.24$ ml/Gm/min, significantly below both fresh controls and the freshly prepared solutions in groups 1,4, and 5. Similarly, comparatively poor function followed simple ice storage with UW for 24 hours without microperfusion, (Control Group (c)). The mean CO in this group was $12.84\pm10.03$ ml/Gm/min ($P<0.01$ vs group (a) and group (1)).

Experimental group (2) in which the UW solution had been shelf stored in plastic bags for 4-6 months, yielded a mean CO significantly lower than with HES-UW made up fresh before use (Experimental Group (1)). It would appear that this effect is due to oxidation of the glutathione during shelf storage.

These data suggest that simple ice storage of the heart with the flush solution generally accepted heretofore to have the best composition (UW solution) yields inadequate function after 24-hour storage. This failure is probably due in part to the accumulation of waste products and the development of acidosis. Although we do not wish to be bound by the following explanation, it appears that low flow rate perfusion and the UW solution and the solution of Experimental Groups 4 and 5 (at rates ranging from 3 to about 6 ml/Gm tissue/24 hours) offers support of anaerobic metabolism by provision of substrate, control of acidosis, and removal of waste products. This process leads to significant improvement in cardiac performance to levels that are either equal to or only a little below fresh unstored controls. In this low flow perfusion method the presence of a colloid appears to be essential. Of the colloids tested, high molecular weight polyethylene glycol yields surprisingly good results and would seem to be the best. Higher rates of perfusion in the presence of oxygen utilizing a modified cardioplegic solution (Control Group (d)) resembling St. Thomas II solution yielded results that were clearly inferior to hypoxic, low flow perfusion. Flow rates of conventional continuous perfusion methods (on the order of 1 ml/Gm/min) are approximately 500 times greater than the flow rates desirably employed utilizing the perfusate of the invention.

TABLE 3

COMPOSITION OF PERFUSION SOLUTIONS

| Substance | Control Group "WP" | Exp. Group (1)&(2) UW | Exp. Group (3) UW. No HES | Exp. Group (4) High MWPEG | Exp. Group (5) High MWPEG |
|---|---|---|---|---|---|
| Na | 126 | 30 | 30 | 30 | 30 |
| K | 8 | 125 | 125 | 125 | 125 |
| Ca | 0.6 | — | — | — | — |
| Mg | 14 | 5 | 5 | 5 | 5 |
| Cl | 127 | — | — | — | — |
| $HCO_3$ | — | — | — | — | — |
| $H_2PO_4$ | 8 | 25 | 25 | 25 | 25 |
| $SO_4$ | 14 | 5 | 5 | 5 | 5 |
| Lactobionate | — | 100 | 100 | 100 | 100 |
| Raffinose | — | 30 | 30 | 30 | 30 |
| Glucose | 11 | — | — | — | — |
| Mannitol | — | — | — | — | — |
| Taurine | 4 | — | — | — | — |
| Glycerol | 136 | — | — | — | — |
| Sucrose | 7 | — | — | — | — |
| Polyethylene glycol[1] | 1 Gm/L | — | — | — | — |
| Chlorpromazine | 0.010 | — | — | — | — |
| Procaine | 1 | — | — | — | — |
| Phenoxybenzamine | 0.007 | — | — | — | — |
| Adenosine | — | 5 | 5 | 5 | 5 |

TABLE 3-continued

COMPOSITION OF PERFUSION SOLUTIONS

| Substance | Control Group "WP" | Exp. Group (1)&(2) UW | Exp. Group (3) UW. No HES | Exp. Group (4) High MWPEG | Exp. Group (5) High MWPEG |
|---|---|---|---|---|---|
| Glutathione | — | 3 | 3 | 3 | 3 |
| Insulin | — | 100 U/L | 100 U/L | 100 U/L | — |
| Penicillin | — | .133 Gm/L | .133 Gm/L | .133 Gm/L | — |
| Dexamethasone | — | 8 mg/L | 8 mg/L | 8 mg/L | — |
| Hydroxyethyl starch[1] | — | 50 Gm/L | — | — | — |
| Allopurinol | — | 1 mg/L | 1 mg/L | 1 mg/L | — |
| Polyethylene glycol[2] | — | — | — | 50 Gm/L | 50 Gm/L |

[1]Mol. wgt. of approximately 8,000 daltons.
[2]Mol. wgt. of approximately 15,000–20,000 daltons.

TABLE 4

| Group | # Reaching 100 cm H$_2$O | Cardiac Output (ml/Gm/min) | Significance |
|---|---|---|---|
| Controls | | | |
| (a) (UW) | 6/6 | 26.48 ± 2.25 | |
| (b) (High MWPEG) | 6/6 | 38.30 ± 2.42 | vs (a) p < 0.01 |
| (c) ((a) + ice stored) | 5/9 | 12.64 ± 10.03 | vs (a) p < 0.01 |
| (d) (Oxygenated perfusion) | 11/11 | 21.19 ± 6.20 | vs (a) NS |
| Experimental Groups | | | |
| (1) UW Fresh | 10/10 | 28.72 ± 7.69 | vs (a) NS |
| | | | vs (b) p < 0.01 |
| (2) UW Shelf stored | 8/16 | 17.29 ± 9.27 | vs (1 & 2) p < 0.01 |
| (3) UW No HES | 2/5 | 11.44 ± 6.24 | vs (1 & 2) p < 0.01 |
| (4) UW with high MW PEG (5%) | 14/14 | 31.52 ± 4.48 | vs (a) p < 0.05 |
| | | | vs (b) p < 0.01 |
| (5) UW with high MW PEG (5%) (less insulin and other ingredients) | 6/6 | 31.67 ± 3.43 | vs (4) NS |
| | | | vs (1) NS |

EXAMPLE 3

The ingredients of the organ preservation solutions of the invention can be varied widely, and compositions of the invention (in distilled water and sterilized by filtration through a 0.2 micron filter) have given good results in a small number of dog kidney and heart experiments, and pig heart experiments. Because of technical difficulties associated with large animal heart preservation studies, the data is qualitative rather than quantitative and involves the ability of the heart to beat vigorously and in some cases sustain the circulation of the animal for a few hours with minimum doses of cardiotonic drugs.

Two dog kidneys have successfully been preserved for 48 hours using low flow perfusion, as described below. In one case, the perfusate was UW containing hydroxyethyl starch (solution of Experimental Group (1) from Example 2) and in the second the solution was the following solution containing 5% high molecular weight polyethylene glycol ("20M", Union Carbide):

| Ingredient | Concentration, mM |
|---|---|
| Potassium lactobionate | 100 |
| KH$_2$PO$_4$ | 25 |
| MgSO$_4$ | 5 |
| Raffinose | 30 |
| NaOH[1] | 30–40 |
| Glutathione (reduced) | 3 |
| PEG, mol. wgt. approx. (15,000–20,000 daltons) | 5 5% by weight |

[1]Added to provide a final pH 24 hours after initial formulation of the solution, in the range of 7.1–7.45.

For each solution, the left kidney was removed from an anesthetized mongrel dog, immediately flushed with 150 ml of the solution and immersed in ice saline. Thereafter, a cannula was tied into the renal artery and the perfusate solution a 0° C. was perfused through the artery for 48 hours using an electrically driven syringe pump at a rate of 3 ml/Gm/24 hours. At the end of this time, the dog was again anesthetized, the contralateral kidney removed and the preserved kidney transplanted into the right side of the pelvis using conventional vascular and ureter-to bladder anastomosis techniques. Blood samples were taken daily for the following week and serum creatinine levels measured. The maximum serum creatinine in the dog receiving the kidney perfused with UW was 3.4 mg % and in the other dog receiving the kidney preserved with the high molecular weight polyethylene glycol solution was 3.0 mg %. This preliminary data suggests that the latter solution may be equally as effective as the UW solution for kidney preservation and that the low flow perfusion technique may be beneficial in the kidney as it has been shown to be for the heart.

While a preferred embodiment of the present invention has been described, it should be understood that various changes, adaptations and modifications may be made therein without departing from the spirit of the invention and the scope of the appended claims.

We claim:

1. An aqueous solution for the preservation of organs comprising at least about 3% by weight of polyethylene glycol having an average molecular weight of at least about 15,000 daltons and being essentially free of material capable of being removed by filtration through a 10 micron filter, and a buffer regulating the pH of the perfusate at a value in the range of 7.1–7.5.

2. The solution of claim 1 in which the polyethylene glycol is present in a concentration in the range of from about 4% to about 10% by weight.

3. The solution of claim 1 wherein at least about 60% by weight of the polyethylene glycol has a molecular weight of at least about 15,000 daltons.

4. The solution of claim 1 wherein the perfusate is essentially devoid of nutrients metabolizable by an organ to be preserved.

5. An organ preservation solution comprising, in aqueous solution, from about 4% to about 10% by weight of polyethylene glycol having an average molecular weight in the range of about 15,000 daltons to about 20,000 daltons, a buffer buffering the pH of the solution to a value in the range of about 7.1 to about 7.5, and an impermeant composition for retarding the passage of water across cell membranes of an organ treated with the solution, the solution being essentially free of material retained by 10 micron filtration.

6. The solution of claim 5 in which the impermeant composition includes sodium or potassium lactobionate.

7. The solution of claim 5 wherein at least about 60% of the polyethylene glycol by weight is of at least about 15,000 daltons molecular weight.

8. An organ preservative comprising, in aqueous solution, from about 4% to about 10% by weight of polyethylene glycol having an average mlecular weight in the range of about 15,000 daltons to about 20,000 daltons, the solution containing the following ingredients in approximately the amounts listed or their equivalents:
(a) NaOH, 30–40 mM,
(b) Lactobionic acid, 100 mM,
(c) $KH_2PO_4$, 25 mM,
(d) KOH, 100 mM,
(e) Raffinose, 30 mM,
(f) Glutathione, 3 mM.

9. Method of preserving an organ intended for transplantation, including the step of contacting the organ with an aqueous solution comprising at least about 3% by weight of polyethylene glycol having an average molecular weight of at least about 15,000 daltons and essentially free of material retained by 10 micron filtration.

10. The method of claim 9 wherein the vascular system of said organ is flushed with the solution immediately prior to harvesting.

11. The method of claim 9 wherein the vascular system of said organ is flushed with the solution immediately following harvesting.

12. The method of claim 9 wherein the organ following harvesting is perfused with the solution at a rate in the range of from about 3 to about 6 ml per gram of organ weight per hour.

13. Method of stopping a mammalian heart to enable surgical procedures to be performed thereon, comprising flushing the heart with an aqueous cardioplegia solution comprising at least about 3% by weight of polyethylene glycol having an average molecular weight of at least about 15,000 daltons, and an impermeant composition for retarding the passage of water across cell membranes of the heart, the cardioplegia solution being essentially free of material retained by 10 micron filtration.

14. The method of claim 13 in which the polyethylene glycol ingredient has an average molecular weight in the range of about 15,000 daltons to about 20,000 daltons, the solution including a buffer buffering the pH of the perfusate to a value in the range of about 7.1 to about 7.5.

15. The method of any of claims 9–12 wherein the method is carried out upon a mammalian heart.

16. Method of preserving a heart organ intended for transplantation which comprises perfusing the heart, at a rate in the range of from about 3 to about 6 ml per gram of heart weight per hour, with an aqueous solution comprising from 4 to 10% by weight of polyethylene glycol having an average molecular weight of at least about 15,000 daltons, the solution having a pH in the range of about 7.1 to about 7.5 and being essentially free of material retained by 10 micron filtration.

* * * * *

UNITED STATES PATENT AND TRADEMARK OFFICE
CERTIFICATE OF CORRECTION

PATENT NO. : 4,938,961
DATED : July 3, 1990
INVENTOR(S) : GEOFFREY COLLINS and WINSTON WICOMB It is certified that error appears in the above—identified patent and that said Letters Patent is hereby corrected as shown below:

In the title, replace "POKYETHYLENE" with --POLYETHYLENE--.

In line 4 of the Abstract, rewrite "polypropylene" as --polyethylene--.

Column 1, line 53, replace "non transplant" with --non-transplant--.

Column 2, line 26, rewrite "ex vivo" as --ex vivo--.

Column 5, line 35, replace "trachesotomy" with --tracheostomy--.

Column 7, line 15, replace " ex vivo" with --ex vivo--.

Column 10, line 44, rewrite "ureter-to bladder" as --ureter-to-bladder--.

Column 11, line 27, rewrite "mlecular" as --molecular--.

Signed and Sealed this

Fourth Day of May, 1993

Attest:

MICHAEL K. KIRK

Attesting Officer

Acting Commissioner of Patents and Trademarks